United States Patent [19]

Bullara

[11] Patent Number: 4,920,979

[45] Date of Patent: May 1, 1990

[54] BIDIRECTIONAL HELICAL ELECTRODE FOR NERVE STIMULATION

[75] Inventor: Leo A. Bullara, Glendora, Calif.

[73] Assignee: Huntington Medical Research Institute, Pasadena, Calif.

[21] Appl. No.: 256,702

[22] Filed: Oct. 12, 1988

[51] Int. Cl.⁵ .............................................. A61N 1/05
[52] U.S. Cl. .................................................... 128/784
[58] Field of Search ............ 128/642, 784, 785, 419 C

[56] References Cited

U.S. PATENT DOCUMENTS

| | | | |
|---|---|---|---|
| 4,573,481 | 3/1986 | Bullara | 128/784 |
| 4,590,946 | 5/1986 | Loeb | 128/785 X |
| 4,602,624 | 7/1986 | Naples et al. | 128/784 |
| 4,750,499 | 6/1988 | Hoffer | 128/784 |

FOREIGN PATENT DOCUMENTS 2525110 10/1983 France ................. 128/785

OTHER PUBLICATIONS

Julien et al., "Electroneurographic Recordings . . . Sets", J. Neuroscience Methods 5, No. 3, Mar. 1982, pp. 267-272.

Primary Examiner—Lee S. Cohen
Attorney, Agent, or Firm—Christie, Parker & Hale

[57] ABSTRACT

A circumneural electrode assembly having a pair of spaced-apart and oppositely directed helical portions which can be opened by an insertion tool to fit the assembly over a peripheral or cranial nerve. One or more conductive electrodes on the inner surfaces of the helical portions intimately contact the nerve surface to deliver electrical stimulating signals, or alternatively, to block nerve conduction or to sense evoked potentials. The surgically implanted assembly is stable in position on the nerve, and is installed with a minimum of nerve manipulation and possible resulting trauma. The assembly preserves the advantages of previously disclosed spiral electrodes, while greatly simplifying installation, particularly in a nerve which is deeply recessed in overlying muscle or arteries.

13 Claims, 2 Drawing Sheets

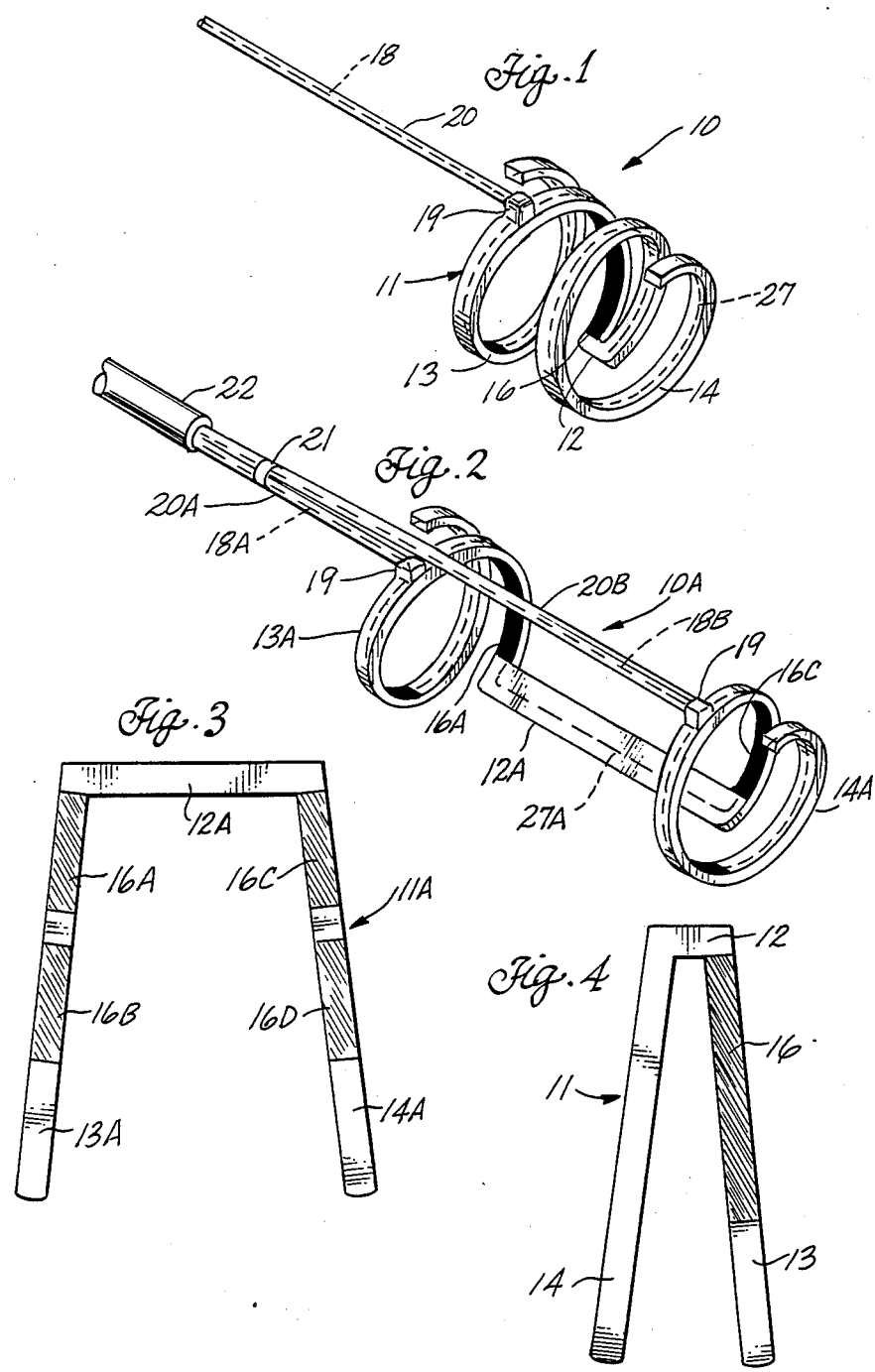

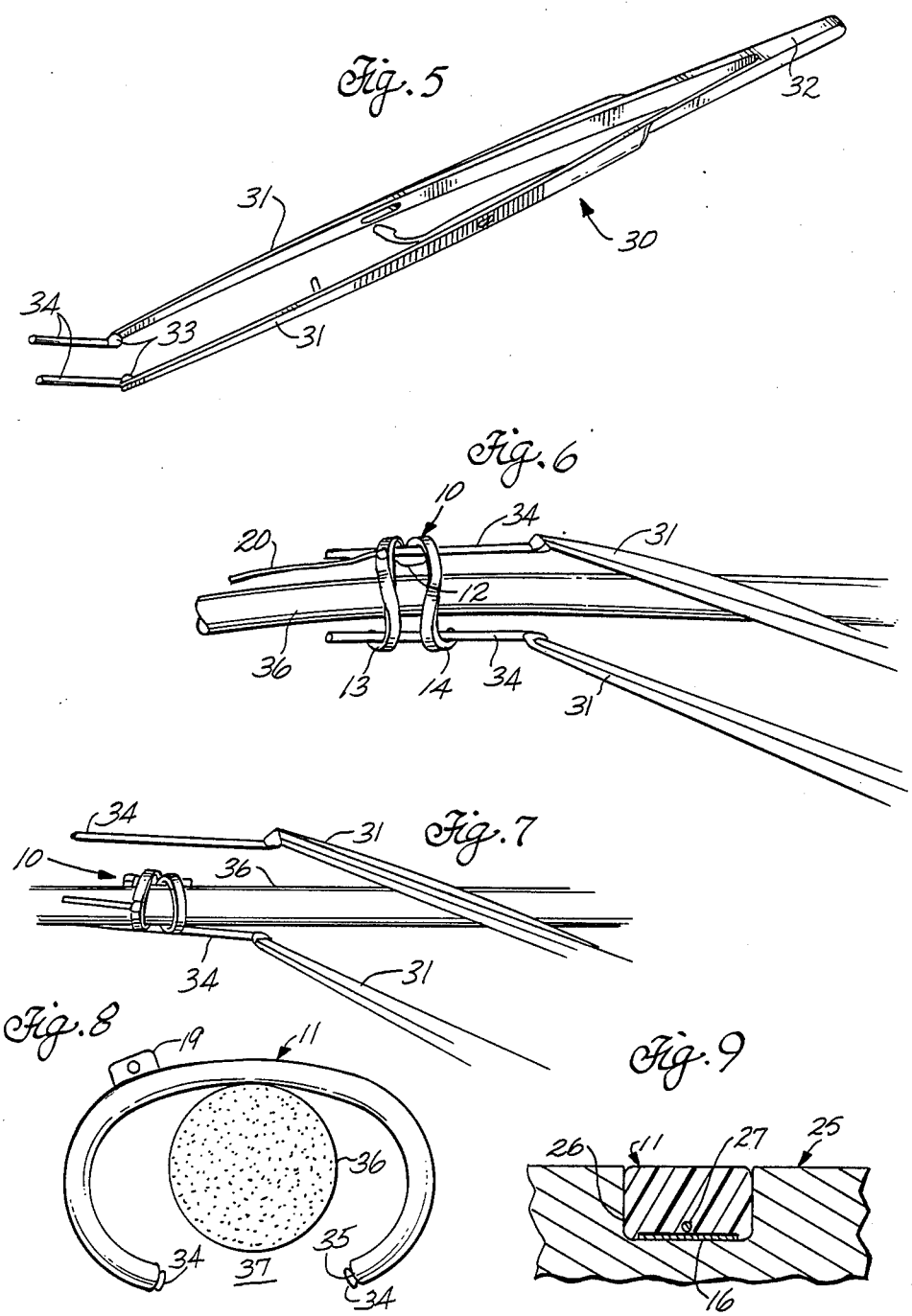

BIDIRECTIONAL HELICAL ELECTRODE FOR NERVE STIMULATION

BACKGROUND OF THE INVENTION

This invention relates to an electrode assembly which is implantable in a human or animal body around a nerve. Typically, the electrode is connected by a wire or wires to an implanted electronic biostimulator which can be remotely programed, or by an electronic circuit commanded by an external wireless telemetry transmitter to deliver electrical signals to the nerve. The thus stimulated nerve in turn causes a reaction in one or more muscles to achieve a desired result, such as bladder control for a patient who has lost normal control due to injury or disease.

My U.S. Pat. No. 4,573,481 (the disclosure of which is incorporated herein by reference) describes in greater detail the various types of nerve-stimulating electrodes (e.g. cuff electrodes) which have been used in the past, and the problems which have been encountered with installation and use of these prior-art units. For brevity, the reader is referred to this patent for further background information.

The aforementioned patent discloses a spiral or helical electrode which solves many of the shortcomings of earlier designs, and is wound around the nerve of interest during surgical installation. Excellent results have been obtained with this electrode, but there are occasions where space around the nerve is limited, and the manipulation of the helix to wind it around the nerve demands skillful and painstaking care by the surgeon.

The electrode assembly (and associated installation tool) of the present invention incorporates the important advantages of my earlier helical design, and provides significant placement simplification and reduction of trauma risk during installation. Broadly, the new assembly is a flexible electrode-supporting matrix forming two oppositely directed helical portions extending from a central bridge or junction. Each helical portion extends circumferentially somewhat more than 360 degrees (typically about 420 to 540 degrees).

During installation, a tweezer-like tool has a pair of pins or tines which are fitted into the open central bore of the helical matrix. The tines are then expanded to distort and open the flexible helices so a laterally open passage is formed along the length of the matrix. The electrode assembly is then fitted over the nerve in a direction generally perpendicular to the length of the nerve. The tines are withdrawn to enable the matrix to close gently around the nerve to place one or more conductive electrodes in intimate contact with the nerve surface. Contrarotation of the several spiral or helical matrix portions provides a further advantage of improved electrode-assembly anchorage and resistance to unwanted movement along the nerve in response to movement of adjacent tissue or skeletal structure.

SUMMARY OF THE INVENTION

The invention is directed to a circumneural electrode assembly which includes a supportive flexible and insulating matrix formed into two oppositely directed helical portions which are centrally joined, and have free outer ends. The helical portions extend circumferentially at least one full turn, and preferably about one-half additional turn, for a total extent in the range of 360 degrees to 720 degrees. A thin and flexible conductive ribbon (preferably surface-roughened platinum) is secured to the inner surface of one of the helical portions, and multiple electrodes can be provided on one or both portions. A connecting wire or cable extends from the electrode and matrix for coupling to an electronic package which is normally implanted elsewhere in the patient's body.

The assembly is hollow, thus providing an open and generally cylindrical central passage throughout its longitudinal extent. A tweezer-like installation tool has a pair of separable pins or slender tines which are closed together for insertion in the central passage. Separation of the tines distorts the flexible matrix and electrode out of the helical shape into an open-sided configuration which permits the assembly to be slipped over the surgically exposed peripheral nerve in a direction generally perpendicular to the length of the nerve. With the assembly fitted over the nerve, the tool is withdrawn, and the assembly resiliently returns to the undistorted helical shape to encircle the nerve with the electrode in conductive contact with the nerve surface.

BRIEF DESCRIPTION OF THE DRAWINGS

FIG. 1 is a pictorial view of a monopolar electrode assembly with closely spaced helical portions;

FIG. 2 is a view similar to FIG. 1, but showing a multipolar electrode assembly with more widely spaced helical portions;

FIG. 3 is a plan view of the electrode assembly of FIG. 2 as distorted into an unwound flat shape;

FIG. 4 is a view similar to FIG. 3, and showing the flattened configuration of the FIG. 1 assembly;

FIG. 5 is a pictorial view of an installation tool for the assembly;

FIG. 6 shows the installation tool fitted and expanded within the electrode assembly to open the helical portions which are positioned for placement over a nerve;

FIG. 7 shows the tool being removed after placement of the assembly around the nerve;

FIG. 8 is an end view of a portion of the assembly as expanded by the tool over the nerve; and FIG. 9 is an enlarged section through one of the helical portions.

DESCRIPTION OF THE PREFERRED EMBODIMENTS

A first embodiment of an electrode assembly 10 according to the invention is shown in FIG. 1. The assembly includes a preformed resilient and insulating matrix 11 having a central junction or bridge portion 12. Two helical portions 13 and 14 extend integrally from the bridge portion, and the helical portions advance away from the bridge portion in opposite directions. Each helical portion extends around at least 360 degrees, and preferably about 420 to 540 degrees. The pitch of the helical turns is small, and adjacent windings are typically spaced apart by less than the axial width of the helical-portion turns, and preferably by about one-third the turn axial width.

Assembly 10 is a monopolar configuration having a single conductive electrode 16 secured on the inner surface of helical portion 13. The electrode is a thin and flexible metal ribbon embedded in the inner matrix surface, but with the inwardly facing surface of the ribbon fully exposed for electrical contact with a nerve. Depending on the type of nerve stimulation desired, the electrode may extend around a full turn of the helical portion, or somewhat less than a full turn as shown in FIG. 1.

A connection means for coupling the electrode to a source (not shown) of electrical signals is formed by a flexible multistrand wire 18 welded to the outer embedded surface of the electrode. The wire extends radially outwardly form the electrode to a small button or dimple 19 integrally formed with helical portion 13. The wire is bent 90 degrees within the dimple to extend parallel to the central axis of the helix, and is insulated by a surrounding tubular jacket 20 joined to the dimple.

FIG. 4 shows the inner surface of assembly 10 when unwound into a flat configuration. This view is provided only for clarifying the assembly structure, and the assembly is not constructed in flat form, nor is it normally distorted or unrolled to this condition during manufacture or use.

The electrode configuration and the spacing of the helical portions can be varied according to the planned nerve-stimulation program, and a typical variation is shown in FIGS. 2 and 3 as an electrode assembly 10A having a matrix 11A. In this second embodiment, bridge portion 12A is significantly lengthened to increase the axial spacing of oppositely directed helical portions 13A and 14A.

Both of these helical portions are provided with a pair of conductive electrodes 16 A-B and 16 C-D, and the electrodes of each pair may be driven by a double lead cable 18A (and 18B for electrodes 16 C-D), depending on the planned nerve-stimulation protocol. The insulated lead-wire jackets 20A and 20B are preferably joined by a drop of adhesive 21 and fitted into a surrounding tubular jacket 22 as they extend away from the assembly. Jacket 22 limits the bending radius of the connecting wire, and helps to prevent kinking, work hardening, and possible eventual breakage of wire strands during body movement.

The inside diameter of the helical portions is selected to be a close or very gently compressive fit on the nerve to be stimulated. Most peripheral nerves which are candidates for electrical stimulation have outside diameters in the range of about 1.0 to 7.0 millimeters, and this accordingly establishes the range of typical inside diameters of the helical portions. When electrodes are provided in both helical portions, bridge portion 12A will typically have an axial length in the range of 7 to 10 mm (though shorter or longer dimensions may be used) for effective stimulation and good evoked response at low power levels.

The supportive matrix of the assembly is preferably formed by a ribbon of medical-grade silicone elastomer, and an acceptable and commercially available uncured formulation is Dow Corning MDX4-4210. The connecting wires should have high flexibility and integrity, and a Teflon-coated 25-strand stainless-steel wire in a silicone-rubber jacket is satisfactory. The electrodes are preferably thin and high-purity annealed platinum ribbons about one millimeter in width and 0.025 mm thick for good flexibility. The ribbon is preferably surface roughened (abrasion with 25 micrometer diamond abrasive is a suitable technique) for increased effective area of the nerve-contacting face, and to enable mechanical bonding with the matrix material.

Prototype electrode assemblies have been made by the methods disclosed in the aforementioned U.S. Pat. No. 4,573,481. Briefly, and with reference to FIG. 9, an arbor or mandrel 25 is provided with a helical groove 26 corresponding in dimension to the desired geometry of the matrix. Each electrode 16 is fitted against the base of the groove, and is securely positioned an pressed against the groove base by a tightly wrapped strand 27 of 5-0 Dacron suture material. Intimate contact of the electrode against the mandrel is important to prevent any flow of silicone elastomer between the facing surfaces. Wire 18 is prewelded to the radially outer surface of the electrode, and the joint is insulated with an epoxy material such as sold under the trademark Epoxylite.

The liquid components of the silicone elastomer are then mixed and degassed to eliminate bubbles, and the elastomer is applied to the mandrel to fill groove 26 which defines the bridge and helical portions of the matrix. The elastomer is cured by heating to complete the formation of the assembly which is then gently stripped away from the mandrel. It is important that the cured matrix have good shape retention combined with high flexibility and resiliency, and the aforementioned silicone elastomer satisfies these requirements.

In a typical configuration, matrix 11 has a generally rectangular cross section, with an axial width of about 1.2 mm, and a radial thickness in the range of about 0.6 to 0.8 mm. The lower end of the thickness range is used for electrode assemblies intended for nerves of small diameter, and the larger thickness is selected for larger nerves to maintain approximately constant radial stiffness of the helical turns.

An installation tool 30 for the electrode assembly is shown in FIG. 5, and the tool is a modified surgical tweezer having a pair of legs 31 extending from a base junction 32 to tips 33. The legs are normally biased apart to separate tips 33, but the tips can be brought together by squeezing the tweezer in conventional fashion.

The tweezer is modified by addition of a pair of tines or pins 34, each of which is welded or brazed to a respective leg tip 33. The pins are parallel, and extend at about 45 degrees from the longitudinal axes of the legs. This angulation permits the pins to be oriented parallel to a nerve as described below, with the tweezer body extending upwardly away from the nerve for manipulation by the surgeon and good visibility of the electrode assembly. The pins are longer than the axial dimension of the electrode assembly to be installed, and are typically about 18 mm long.

Although the pins may have a simple circular cross section, a preferred trough-shaped cross section is shown in FIG. 8. The concave side of this cross section forms a shallow depression or seat 35 to receive the circumferential ends of the helical portions (or the corresponding end of the matrix bridge portion), and thus to support the opened electrode during the installation procedure described below. The trough-shaped cross section also minimizes pin size for fitting within helical assemblies of very small inside diameter.

Referring to FIGS. 6-7, a peripheral nerve 36 is surgically exposed in preparation for installation of electrode assembly 10. Pins 34 of the installation tool are compressed together by squeezing the tweezer, and the adjacent pins are slipped through the hollow interior of the helical electrode assembly. Gripping force on the tweezer is then relaxed, permitting the pins to separate and thereby open the electrode assembly so it can be lowered over nerve 36 as shown in FIG. 6.

Tool 30 is initially positioned within the electrode assembly such that when the pins are separated, one pin will be close to bridge portion 12, and the other pin will be adjacent the free ends of helical portions 13 and 14.

The resulting unwrapping or unwinding of flexible matrix 11 and associated electrode or electrodes opens the helical turns to form a laterally open passage 37 to receive the nerve as shown in FIG. 8.

When the spread electrode assembly has been placed over the top of the nerve, the tweezer pins can be moved toward each other beneath the nerve, and continued lowering of the tweezer tips withdraws the pins from within the electrode. The tweezer is then sufficiently reopened to provide clearance between the pins and the nerve so the tool can be withdrawn.

When the tool pins are removed, the shape memory of resilient matrix 11 causes an automatic self-closing action of helical portions 13 and 14 around nerve 36. The preferred slight compressive fit of the helical portions places the electrode or electrodes in the desired intimate contact with the nerve for good electrical conduction of stimulating signals.

In some implantations of the electrode assembly, there may be only a very slight clearance between the undersurface of the nerve and the underlying body structure. In this situation, the electrode assembly is fitted over the nerve as already described, and the tool pins are then compressed together and gently withdrawn from the electrode matrix by a sideways movement parallel to the nerve axis. The tips are then again spread sufficiently to be withdrawn over the opposed sides of the nerve.

Separation of the installation-tool pins within the helical portions causes unwinding of the helical turns by a sliding movement of the matrix inner surface on the pins. Preferably, the pins are Teflon coated to minimize frictional resistance to this sliding motion of the silicone-rubber matrix over the pins.

In common with the helical electrode of my earlier aforementioned patent, the new electrode assembly has the significant advantages of minimum interference with desirable fluid exchange between the nerve and surrounding tissue, and minimum risk of excessive nerve compression which can cause nerve damage. The new assembly is even more capable of resiliently accommodating nerve swelling or edema resulting from the implantation surgery. Similarly, the assembly has good longitudinal flexibility to accommodate bending of the associated nerve during limb articulation or other body movement. Good electrical contact of the electrode and nerve is also achieved, with little risk of tissue-ingrowth problems encountered with cuff electrodes.

The oppositely directed turns of the helical portions provide an important advantage of good assembly anchorage and resistance to axial movement of the assembly along the nerve in response to adjacent muscle movement or limb articulation. The anchoring effect arises from an opening separation of the distal helical portion which reduces the matrix inside diameter to increase the gripping action of the matrix around the nerve. The tight pitch of the helical portions, and the capability of using multiple electrodes, enables use of multiple stimulus sites along and around the nerve for selective stimulation of nerve bundles.

Apart from these important features, an outstanding advantage of the new assembly is ease of installation, and freedom from any need to wind the assembly manually around the nerve. In addition to reducing surgical manipulation and possible nerve trauma, the simple open-lower-close installation sequence permits placement even when the exposed nerve is deeply recessed in the body with very small undersurface clearance.

Although described above in terms of an assembly with two helical portions of opposite rotation direction, the invention extends to a single helical portion which is useful where axial exposure of the nerve is limited. In both configurations, the helical turn extends around at least 360 degrees to provide complete encirclement of the nerve, and preferably about one-half turn beyond a full circle. If desired, the electrode ribbon may extend along the entire inner circumference of the helical matrix to provide constant stiffness, and any unwanted conductive contact is avoided by applying an insulating coating (Epoxylite is suitable) to portions of the exposed electrode surface.

The extent of the matrix helical turn is preferably kept less than two full turns for several reasons. First, a greater circumferential extent of the helical portion requires a greater separation of the installation-tool pins to open the assembly for fitting over the nerve, and this separation should be minimized so the tool pins can be fitted within a narrow incision. A second factor is to limit distortion of the electrode ribbon which may decrease the desired intimate contact of the electrode against the nerve surface.

There has been described an electrode assembly which incorporates the important advantages of my earlier design, while offering a significant improvement in ease of installation over a nerve to be electrically stimulated.

What is claimed is:

1. An electrode assembly for implantation on a nerve, comprising:
    a flexible supporting matrix of dielectric material, the matrix forming a pair of spaced-apart and oppositely directed helical portions, each helical portion extending circumferentially at least 360 degrees and less than 720 degrees;
    a flexible, conductive electrode secured to an inner surface of one of the helical portions; and
    a flexible connection means connected to the electrode and extending from the matrix for connection to an electronic device;
    the assembly having a central passage longitudinally therethrough and sized to conform to the external dimension of the nerve, whereby a tool can be inserted in the passage to expand the helical portions to open a lateral passage along the full length of the assembly to enable the assembly to be fitted over and closed upon the nerve.

2. The assembly defined in claim 1 wherein the helical portions each have adjacent turns which are spaced apart less than the axial width of the matrix to minimize the axial length of the assembly while providing space between the adjacent turns to permit fluid passage to the nerve.

3. The assembly defined in claim 1 wherein the helical portions are joined by a matrix bridge portion which extends generally parallel to a central axis of the helical portions.

4. The assembly defined in claim 1 wherein a flexible conductive electrode is secured to the inner surface of each helical portion, and the connection means comprises stranded wires secured to the respective electrodes and extending from the outer surface of the respective helical portions.

5. The assembly of claim 1 wherein each helical portion extends circumferentially about one and one-half turns.

6. The assembly of claim 1 wherein each helical portion extends circumferentially in the range of about 420 to 540 degrees.

7. The combination comprising:
an electrode assembly for implantation on a nerve, the assembly comprising:
a flexible supporting matrix of dielectric material, the matrix forming a helix with at least one turn and less than two turns, the helix having a central passage longitudinally therethrough and sized to conform to the external dimension of the nerve;
a flexible conductive electrode secured to an inner surface of the matrix helix;
a flexible connection means connected to the electrode and extending from the matrix for connection to an electronic device; and
an insertion tool having a portion which is fitted and expanded within the central passage to expand the helical portion and thereby to form a laterally open passage along the length of the assembly so the assembly can be fitted over and closed upon the nerve upon removal of the tool portion.

8. The combination defined in claim 7 wherein the insertion tool has a pair of separable legs, each leg having a free end defining a pin, the pins being generally parallel and juxtaposed when the legs are moved toward each other so the pins can be inserted and expanded within the electrode assembly.

9. The combination defined in claim 8 wherein the tool pins are oriented at an angle to longitudinal axes of the respective legs.

10. The combination defined in claim 9 wherein the angle is about 45 degrees.

11. The combination defined in claim 8 wherein each pin defines a concave depression for receiving the matrix.

12. A method for installing a flexible and hollow helical electrode assembly around a nerve, the helical assembly having non-overlapping turns, comprising the steps of:
a. expanding the electrode assembly to open a lateral passage generally parallel to a central axis of the assembly, the passage being of sufficient size to accommodate the nerve;
b. moving the expanded assembly in a direction toward the nerve so the nerve passes through the passage;
c. permitting the electrode assembly to return to a helical configuration around the nerve.

13. The method defined in claim 12 wherein the expanding step is performed with a tool having a pair of pins which are movable together for fitting within the hollow assembly, the pins then being movable away from each other to expand the assembly and thereby to form the lateral passage.

* * * * *